(12) United States Patent
Yoon et al.

(10) Patent No.: US 6,313,299 B1
(45) Date of Patent: Nov. 6, 2001

(54) QUINOLONE CARBOXYLIC ACID DERIVATIVES

(75) Inventors: Sung-Joon Yoon, Seoul; Yong-Ho Chung, Kyunggi-do; Chi-Woo Lee, Kyunggi-do; Yoon-Seok Oh, Kyunggi-do; Nam-Doo Kim, Inchon; Jae-Kyung Lim, Kyunggi-do; Yoon-Ho Jin, Seoul, all of (KR)

(73) Assignee: Dong Wha Pharmaceutical Industrial Co., Ltd., Seoul (KR)

( * ) Notice: Subject to any disclaimer, the term of this patent is extended or adjusted under 35 U.S.C. 154(b) by 0 days.

(21) Appl. No.: 09/446,697

(22) PCT Filed: Jun. 26, 1998

(86) PCT No.: PCT/KR98/00185

§ 371 Date: Dec. 23, 1999

§ 102(e) Date: Dec. 23, 1999

(87) PCT Pub. No.: WO99/00393

PCT Pub. Date: Jan. 7, 1999

(30) Foreign Application Priority Data

Jun. 26, 1997 (KR) .................................................. 97-27806
Jan. 20, 1998 (KR) .................................................. 98-1609

(51) Int. Cl.$^7$ ......................... C07D 487/10; A61K 31/47
(52) U.S. Cl. ............................................. 546/18; 514/278
(58) Field of Search ............................... 546/18; 514/278

(56) References Cited

U.S. PATENT DOCUMENTS

| | | | |
|---|---|---|---|
| 4,146,719 | 3/1979 | Irikura | 544/363 |
| 4,556,658 | 12/1985 | Grohe et al. | 514/254 |
| 4,617,308 | 10/1986 | Mich et al. | 514/312 |
| 4,620,007 | 10/1986 | Grohe et al. | 546/156 |
| 4,638,067 | 1/1987 | Townley et al. | 546/15 |
| 4,670,444 | 6/1987 | Grohe et al. | 514/300 |
| 4,704,459 | 11/1987 | Todo et al. | 546/123 |
| 5,496,947 | 3/1996 | Yoon et al. | 544/362 |

FOREIGN PATENT DOCUMENTS

| | | |
|---|---|---|
| 0153165 | 8/1985 | (EP) . |
| 0357047 | 3/1990 | (EP) . |
| 0529688 | 3/1993 | (EP) . |
| 0550025 | 7/1993 | (EP) . |
| 0643058 | 3/1995 | (EP) . |
| 0722941 | 7/1996 | (EP) . |
| 62-174053 | 7/1987 | (JP) . |

OTHER PUBLICATIONS

T. Kametani, vol. 34, No. 12, Scientific Technical Information Center Dec. 22, 1992, pp. 2301–2311.

*Primary Examiner*—Alan L. Rotman
(74) *Attorney, Agent, or Firm*—Birch, Stewart, Kolasch & Birch, LLP

(57) ABSTRACT

The present invention relates to quinolonecarboxylic acid derivatives having more excellent and broad antibacterial activities than the existing quinolone-series antibiotics. More specifically, it pertains to novel quinolonecarboxylic acid derivatives represented by following formula 1, which have a derivative of 7-[8-(alkoxyimino)-2,6-diazaspiro[3.4]oct-6-yl] as a substituent, and pharmaceutically acceptable salts and isomers thereof:

Wherein, A is C—H, C—F, C—Cl, C—O—CH$_3$ or N; Y is H or amino; R$_1$ is cyclopropyl or 2,4-difluorophenyl; R$_2$ is C$_{1-4}$ alkyl; and R$_3$ is H or C$_{1-4}$ alkyl.

3 Claims, No Drawings

QUINOLONE CARBOXYLIC ACID DERIVATIVES

This application is the national phase under 35 U.S.C. §371 of PCT International Application No. PCT/KR98/00185 which has an International filing date of Jun. 26, 1998, which designated the United States of America.

FIELD OF THE INVENTION

The present invention relates to quinolonecarboxylic acid derivatives having more excellent and broad antibacterial activities than the existing quinolone-series antibiotics. More specifically, it pertains to novel quinolonecarboxylic acid derivatives represented by following formula 1, which have a derivative of 7-[8-(alkoxyimino)-2,6-diazaspiro[3.4] oct-6-yl] as a substituent, and pharmaceutically acceptable salts and isomers thereof:

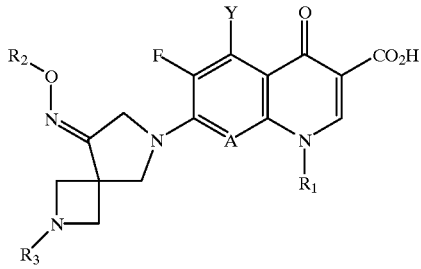

1

Wherein, A is C—H, C—F, C—Cl, C—O—CH$_3$ or N; Y is H or amino; R$_1$ is cyclopropyl or 2,4-difluorophenyl; R$_2$ is C$_{1-4}$ alkyl; and R$_3$ is H or C$_{1-4}$ alkyl.

BACKGROUND OF THE INVENTION

Quinolonecarboxylic acid derivatives are synthetic antibiotics which are well known to be useful for the treatment of infective diseases in human and animals due to their potent and broad antibacterial activities. Quinolone-series antibiotics such as norfloxacin, ofloxacin and ciprofloxacin are currently used very usefully for the treatment of human diseases and their efficacies are acknowledged. However, these medicines have a problem that: even though they show excellent antibacterial activities against gram-negative bacteria, they still show ordinary or relatively low antibacterial activities against gram-positive bacteria. Accordingly, there have been various studies for solving such problems of existing quinolone-series antibiotics and, finally, sparfloxacin having improved antibacterial activities against gram-positive bacteria has been developed.

However, this compound still shows weak antibacterial activities against Streptococci, methicillin resistant *Staphylococcus aureus*(MRSA) and other currently increasing quinolone-resistant strains. These strains are well known as pathogens of the respiratory infections. Therefore, there are increasing needs for the development of improved quinolone antibiotics which exhibit excellent antibacterial activities against such quinolone-resistant strains.

On the other hand, Korean patent laid-open publication Nos. 96-873, 96-22501 and 96-22502, and EP688772A1 disclose quinolone-series antibacterial agents of following formulae 16, 17 and 18:

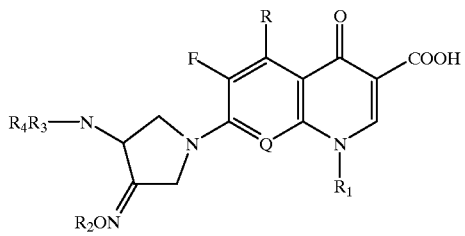

16

Wherein, Q is C—H, C—F, C—Cl, C—OH, C—O—CH$_3$ or N; R is H, methyl or amino; R$_1$ is cyclopropyl, ethyl, or phenyl substituted with more than one fluorine atom; R$_2$ is H, C$_{1-4}$ straight or branched alkyl, phenyl or allyl.

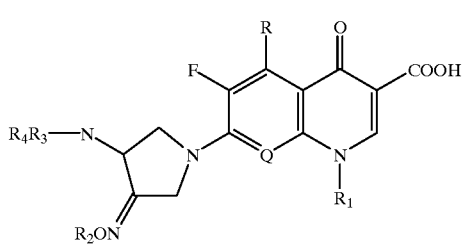

17

Wherein, R is H, methyl or amino; Q is C—H, C—F, C—Cl, C—CH$_3$. C—O—CH$_3$ or N; R$_1$ is cyclopropyl, ethyl, or phenyl substituted with one or more fluorine atoms; R$_2$ is C$_3$–C$_4$ branched alkyl such as t-butyl and cyclopropylmethyl, C$_3$–C$_6$ alkyl having a triple bond such as propagyl and homopropagyl, 2-haloethyl, methoxymethyl, methoxycarbonylmethyl, or a group having the following formula:

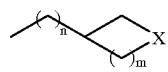

Wherein, n is 0 or 1; m is 0, 1 or 2; x is methylene, 0 or N; R$_3$ and R$_4$ are independently H or C$_1$–C$_3$ alkyl group, or they may form a ring with a nitrogen group to which they are attached.

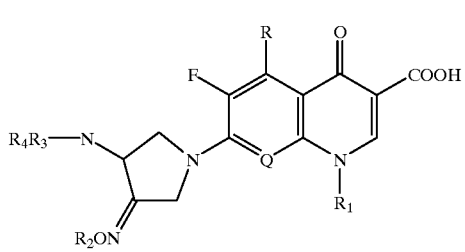

18

Wherein,

R is H, methyl or amino group;

Q is C—H, C—F, C—Cl, C—CH$_3$, C—O-CH$_3$ or N;

R$_1$ is cyclopropyl, ethyl, or phenyl group substituted with one or more fluorine atom;

$R_2$ is a group of following formula a:

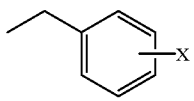
a

Wherein, X is 2-, 3- or 4-fluoro, cyano, nitro, methoxy, methyl or $C_2$–$C_4$ alkyl group, or 2,4-difluro group: a group of following formula b:

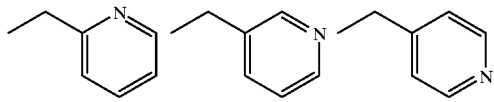
b or an arylmethyl group containing a hetero group of following formula

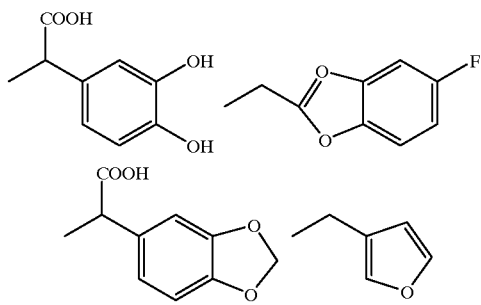
c $R_3$ and $R_4$ are independently H or $C_1$–$C_3$ alkyl group, or they may form a ring with a nitrogen group to which they are attached.

The above compounds are different from the compound of the present invention of the formula 1 in their structures. Specifically, in the compounds disclosed in Korean Patent laid-open publication Nos. 96-873, 96-22501 and 96-22502, and EP688772 A1, an alkoxyimino group is substituted on the pyrrolidine ring, which is a substituent at the 7-position, and the substituents adjacent to the alkoxyimino group such as amino, alkylamino, aminomethyl, alkylaminomethyl are attached to the pyrrolidine ring as a straight chain form. In contrast, in the compounds of the present invention, the pyrrolidine ring substituted at the 7-position having an oxime and its derivatives, forms a diazaspiro compound with an azetidine structure. Accordingly, the compounds of the present invention are different from those of the above patent laid-open publications in their structures. In terms of antibacterial activities, the compounds of the present invention show strong antibacterial activities against the recently-increasing quinolone-resistant strains, while the compounds of the above patent laid-open publications exhibit very weak antibacterial activities against the quinolone-resistant strains.

Further, although EP265230 A1 discloses the substitution of diazaspiro compound at 7-position of the quinolone derivative, it specifically discloses only 2,7-diazaspiro[4,4] nonane and 2-methyl-2,7-diazaspiro[4,4]nonane compounds of the following formulae

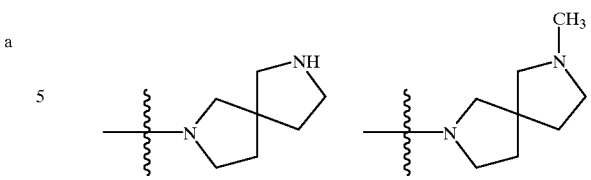

and does not specifically disclose 2,6-diazaspiro[3,4]octane compound as disclosed in the present invention. Moreover, there is no mention about the alkoxyimino group introduced in the 2,6-diazaspiro[3,4]octane substituent on the 7-position as disclosed in the present invention. Accordingly, the compounds of the present invention are different from those of the above-mentioned patent laid-open publications in terms of structure. As to antibacterial activities, the compounds of the present invention exhibit excellent antibacterial activities against the existing quinolone-resistant strains as well as against both of gram-negative and gram-positive bacteria, while the compounds of the above-mentioned patent laid-open publications have ordinary antibacterial activities against gram-negative and gram-positive bacteria.

The present inventors have endeavored constantly to develop novel quinolonecarboxylic acids which exhibit excellent antibacterial activities against both of gram-negative and gram-positive bacteria, as well as improved antibacterial activities against such problematic strains as Streptococci, methicillin resistant *Staphylococcus aureus* (MRSA) and other currently increasing quinolone-resistant strains.

Finally, the present inventors have accomplished the present invention by discovering that quinolonecarboxylic acids substituted with 7-[8-(alkoxyimino)-2,6-diazaspiro[3,4]oct-6-yl] at the 7-position show excellent antibacterial activities against the above-mentioned strains.

SUMMARY OF THE INVENTION

Accordingly, it is an object of the present invention to provide novel quinolonecarboxylic acid derivatives of the above formula 1, and pharmaceutically acceptable salts and isomers thereof, which exhibit excellent antibacterial activities against both of gram-negative and gram-positive bacteria and, especially, show superior antibacterial activities against the methicillin-resistant strains, as well as against the existing quinolone-resistant strains.

Another object of the present invention is to provide processes for preparing the novel quinolonecarboxylic acid derivatives of the formula 1.

DETAILED DESCRIPTION OF THE INVENTION

The present invention is characterized by quinolonecarboxylic acid derivatives represented by following formula 1, and pharmaceutically acceptable salts and isomers thereof:

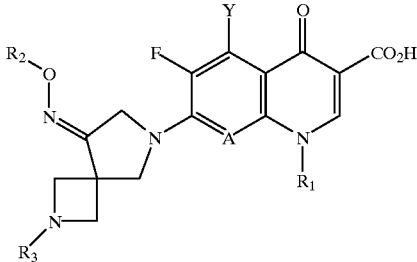

Wherein, A is C—H, C—F, C—Cl, C—O—CH$_3$ or N; Y is H or amino; R$_1$ is cyclopropyl or 2,4-difluorophenyl; R$_2$ is C$_{1-4}$ alkyl; and R$_3$ is H or C$_{1-4}$ alkyl.

The present invention is described in more detail as follows.

According to the present invention, the typical examples of quinolone carboxylic acid derivatives of the above formula 1 may be listed as follows:

1-cyclopropyl-6-fluoro-7-[8-(methoxyimino)-2,6-diazaspiro[3,4]oct-6-yl]-1,4-dihydro-4-oxo-1,8-naphthyridine-3-carboxylic acid, 1-cyclopropyl-6-fluoro-7-[8-(methoxyimino)-2,6-diazaspiro[3,4]oct-6-yl]-1,4-dihydro-4-oxo-quinoline-3-carboxylic acid, 1-cyclopropyl-6,8-difluoro-7-[8-(methoxyimino)-2,6-diazaspiro[3,4]oct-6-yl]-1,4-dihydro-4-oxo-quinoline-3-carboxylic acid, 1-cyclopropyl-6-fluoro-8-chloro-7-[8-(methoxyimino)-2,6-diazaspiro[3,4]oct-6-yl]-1,4-dihydro-4-oxo-quinoline-3-carboxylic acid, 1-cyclopropyl-5-amino-6,8-difluoro-7-[8-(methoxyimino)-2,6-diazaspiro[3,4]oct-6-yl]-1,4-dihydro-4-oxo-quinoline-3-carboxylic acid, 1-(2,4-difluorophenyl)-6-fluoro-7-[8-(methoxyimino)-2,6-diazaspiro[3,4]oct-6-yl]-1,4-dihydro-4-oxo-quinoline-3-carboxylic acid, 1-(2,4-difluorophenyl)-6-fluoro-7-[8-(methoxyimino)-2,6-diazaspiro[3,4]oct-6-yl]-1,4-dihydro-4-oxo-1,8-naphthyridine-3-carboxylic acid, 1-cyclopropyl-6-fluoro-7-[8-(ethoxyimino)-2,6-diazaspiro[3,4]oct-6-yl]-1,4-dihydro-4-oxo-1,8-naphthyridine-3-carboxylic acid, 1-cyclopropyl-5-amino-6,8-difluoro-7-[8-(ethoxyimino)-2,6-diazaspiro[3,4]oct-6-yl]-1,4-dihydro-4-oxo-quinoline-3-carboxylic acid, 1-cyclopropyl-6-fluoro-7-[8-(methoxyimino)-2-methyl-2,6-diazaspiro[3,4]oct-6-yl]-1,4-dihydro-4-oxo-1,8-naphthyridine-3-carboxylic acid, 1-cyclopropyl-6-fluoro-7-[8-(methoxyimino)-2-methyl-2,6-diazaspiro[3,4]oct-6-yl]-1,4-dihydro-4-oxo-quinoline-3-carboxylic acid, 1-cyclopropyl-6,8-difluoro-7-[8-(methoxyimino)-2-methyl-2,6-diazaspiro[3,4]oct-6-yl]-1,4-dihydro-4-oxo-quinoline-3-carboxylic acid, 1-cyclopropyl-6-fluoro-8-chloro-7-[8-(methoxyimino)-2-methyl-2,6-diazaspiro[3,4]oct-6-yl]-1,4-dihydro-4-oxo-quinoline-3-carboxylic acid, and 1-cyclopropyl-5-amino-6,8-difluoro-7-[8-(methoxyimino)-2-methyl-2,6-diazaspiro[3,4]oct-6-yl]-1,4-dihydro-4-oxo-quinoline-3-carboxylic acid.

The quinolonecarboxylic acid derivatives of the present invention represented by formula 1 have a double bond in the pyrrolidine ring at the 7-position and, accordingly, geometric isomers of cis- or trans-form may be present. The present invention includes all of such geometric isomers.

A pharmaceutically acceptable salts may be prepared from the quinolonecarboxylic acid derivatives of the present invention represented by formula 1, in accordance with some ordinary methods in the art to which the present invention pertains. As one kind of such salts, an acid addition salt may be prepared, and exemplary acids to be used therefor include an inorganic acid such as hydrochloric acid, phosphoric acid and sulfuric acid; and an organic acid such as methane sulfonic acid, p-toluene sulfonic acid, acetic acid, citric acid, maleic acid, succinic acid, oxalic acid, benzoic acid, tartaric acid, fumaric acid, manderic acid and glucuronic acid. In addition, a cation such as sodium or potassium ion may also be used for the preparation of pharmaceutically acceptable salts.

Further, the present invention includes the process of preparing the quinolonecarboxylic acid derivatives represented by formula 1.

The quinolonecarboxylic acid derivatives of the present invention of the formula 1 may be prepared by any one of two methods represented by following Reaction schemes 1 and 2.

In the following reaction scheme 1, the compound of following formula 2 is subjected to coupling reaction with the compound of following formula 3 to obtain the desired compound of the present invention, i.e., a quinolonecarboxylic acid derivative represented by following formula 1.

[Reaction scheme 1]

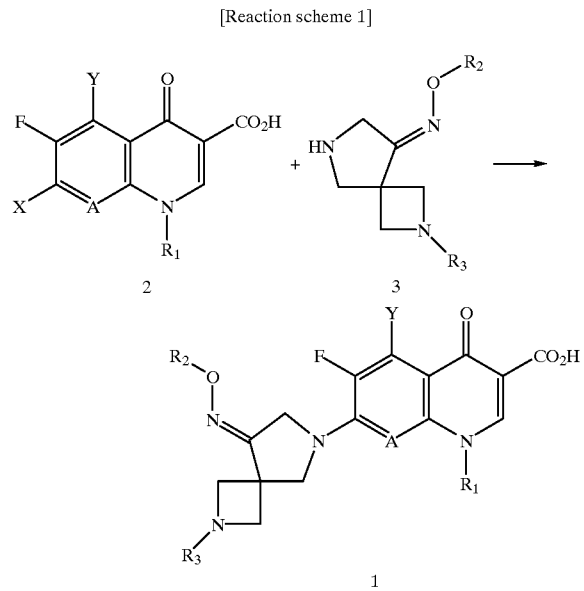

Wherein, A, Y, R$_1$, R$_2$ and R$_3$ are respectively as definded above, and X is a halogen atom, preferably, fluorine or chlorine. The compound of formula 2 may be prepared in accordance with the method described in U.S. Pat. No. 4,382,892. The compound of formula 3 may be used in the form of a free base or an acid salt, and the acid salt may be formed by using an acid such as hydrochloric acid, acetic acid and trifluoroacetic acid.

To explain the above reaction scheme in more detail, the coupling reaction of the compound of formula 2 with the compound of formula 3 are carried out under the presence of a solvent with the addition of a suitable base (acid acceptor) to obtain a quinolonecarboxylic acid derivative represented by formula 1. The reaction may be completed preferably at 0 to 200° C. for 1 to 24 hours with stirring.

As the solvent used in the above reaction, acetonitrile, dimethyl formamid(DMF), dimethylsulfoxide(DMSO) and pyridine are preferred. As the base(acid acceptor), it is preferred to use inorganic bases such as sodium hydrogencarbonate, calcium carbonate, and sodium carbonate, or organic bases such as triethylamine, diisopropylethylamine, pyridine, lutidine, N,N-dimethylaniline, N,N-dimethylaminopyridine, 1,8-diazabicyclo[5,4,0]undec-7-ene(DBU), 1,5-diazabicyclo[4,3,0]nonene-5(DBN), and 1,4-diazabicyclo[2,2,2]octane (DABCO). Further, the reaction efficiency may be increased by using an excessive amount (2 to 10 mole equivalents) of the compound of formula 3 as an acid acceptor. The reaction rate may increase by using an ion-exchange resin. Exemplary ion-exchange resin may include Amberlite® IRA-420, Amberlite® IRA-900 and Amberlite® IRA-64.

In the second preparation process(Reaction scheme 2), the compound of following formula 2 is subjected to coupling reaction with the compound of following formula 3a to prepare the desired compound of the present invention, i.e., a compound represented by following formula 1 wherein $R_3$ is H, via an intermediate of following formula 4. Further, the compounds of formula 1 wherein $R_3$ is $C_{1-4}$ alkyl may be prepared by reductive alkylation of the compounds of formula 1 wherein $R_3$ is H with lower aldehydes.

[Reaction scheme 2]

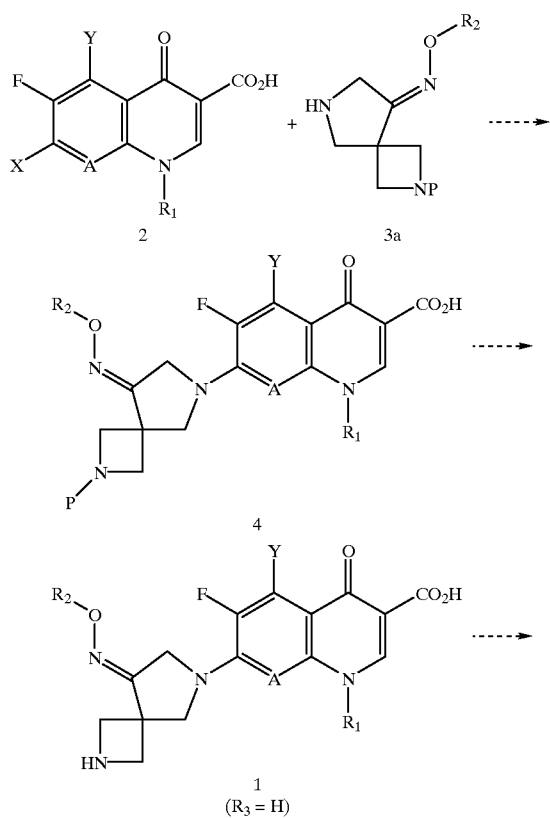

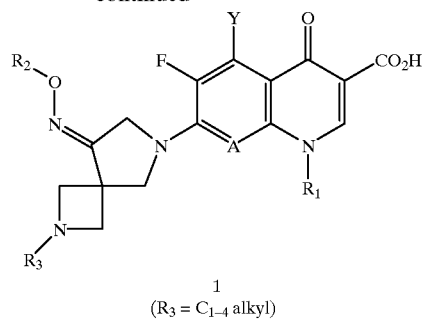

Wherein, A, X, Y, $R_1$, $R_2$ and $R_3$ are respectively as definded above, and P is an amine protecting group.

The compound of formula 3a may be used in the form of a free base or an acid salt, and the acid salt may be formed by using an acid such as hydrochloric acid, acetic acid and trifluoroacetic acid. Further, exemplary amine protecting groups(P) of the compound of formula 3a include formyl, acetyl, trifluoroacetyl, benzoyl, alkoxycarbonyl(e.g., ethoxycarbonyl, t-butoxycarbonyl, benzyloxycarbonyl, p-methoxybenzyloxycarbonyl, trichloroethoxycarbonyl), benzyl, p-methoxybenzyl and trityl.

The above reaction is carried out under the same condition as illustrated in Reaction scheme 1 for the coupling reaction of the compound of formula 2 with the compound of formula 3. The amine protecting group(P) of the compound of formula 4 thus obtained from the condensation reaction is removed by an alkali hydrolysis or a general deprotection reaction to obtain the compound of formula 1.

For example, the compound of formula 4 is reacted in a solvent under the presence of an acid or base at a temperature ranging from room temperature to 120° C. to remove the amine protecting group(P). As an acid for use in the deprotection reaction, an inorganic acid such as hydrochloric acid, bromic acid and sulfuric acid, or an organic acid such as acetic acid, trifluoroacetic acid, formic acid, p-toluenesulphonic acid may be used. Further, in case that the amine protecting group(P) is a benzyl, p-methoxybenzyl, benzyloxycarbonyl, p-methoxybenzyloxycarbonyl or trichloroethoxycarbonyl group, the amine protecting group (P) may be removed by the reduction under the hydrogen atmosphere at a temperature ranging from 5 to 100° C. using palladium, Raney nickel or platinum.

On the other hand, the compounds of formula 1 wherein $R_3$ is $C_{1-4}$ alkyl may be prepared by reductive alkylation of the compounds of formula 1 wherein $R_3$ is H with $C_{1-4}$ aldehyde under a weak acidic condition by using sodium-cyanoborohydride as a reducing agent at 0 to 50° C.

The compounds of formulae 3 and 3a, which are also the starting materials of the present invention, may be prepared by the following Reaction scheme 3.

[Reaction scheme 3]

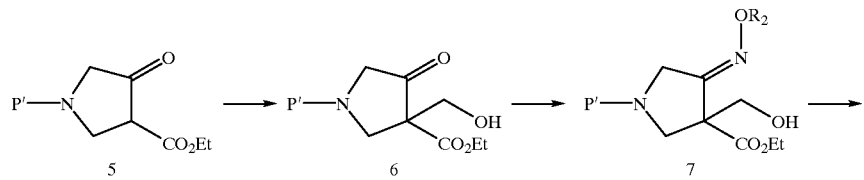

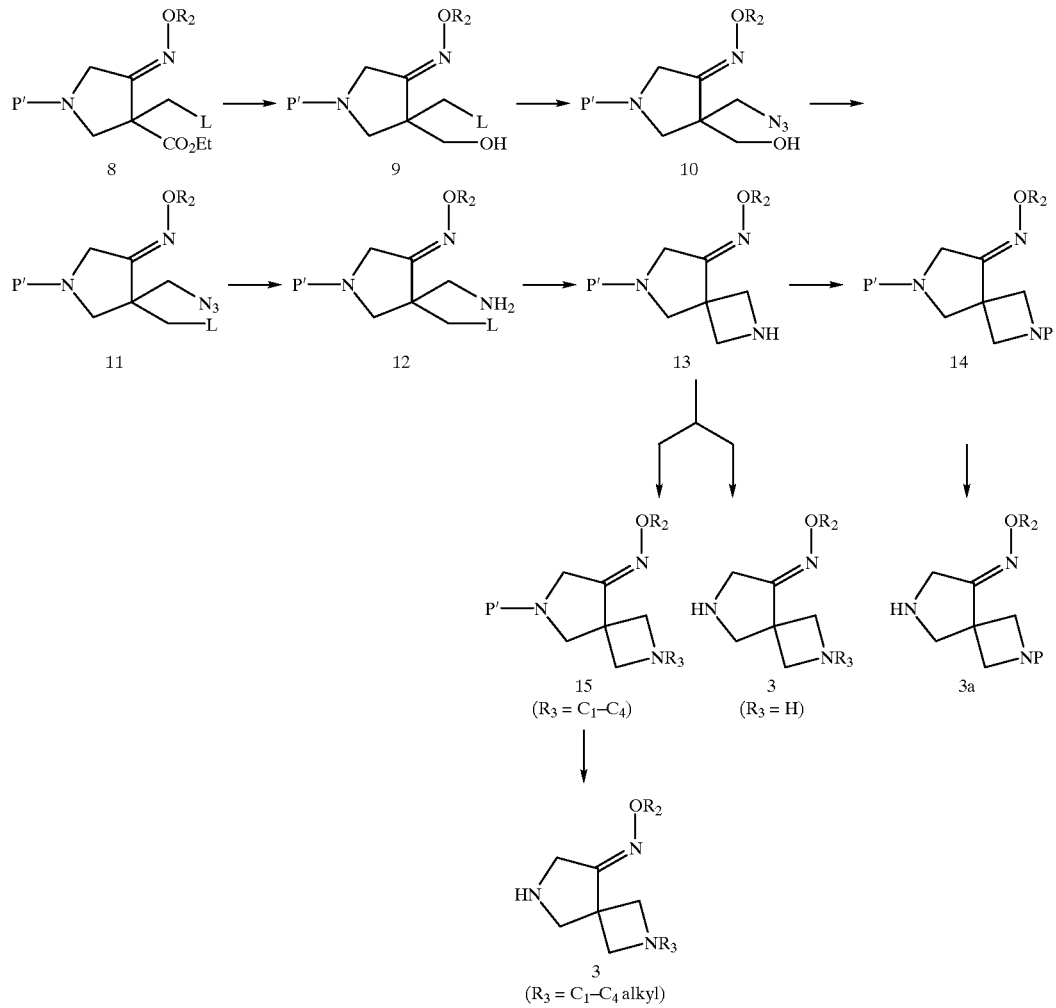

Wherein, $R_2$ and $R_3$ are as defined above; L is methanesulfonyloxy, p-toluenesulfonyloxy, or halogen, preferably fluorine or chlorine; and P' is an amine protecting group such as formyl, acetyl, trifluoroacetyl, benzoyl, alkoxycarbonyl(e.g., ethoxycarbonyl, t-butoxycarbonyl, benzyloxycarbonyl, p-methoxybenzyloxycarbonyl, trichloroethoxycarbonyl), benzyl, p-methoxybenzyl and trityl.

To explain the process of Reaction scheme 3 in detail, a ketoester compound(formula 5) is reacted with an aqueous formalin solution at 0 to room temperature under the presence of a base to obtain a hydroxyketone compound(formula 6). Suitable bases for this reaction include sodium carbonate, calcium carbonate, sodium hydrogen carbonate, sodium hydroxide and calcium hydroxide, and suitable solvents include alcohols such as methanol, ethanol and isopropyl alcohol. The compound of formula 6 is reacted with an alkoxylamine to obtain an alkoxyimino pyrrolidine derivative compound of formula 7 in high yields. In this reaction, pyridine may be used as a solvent, as well as a base. Further, in case that water, tetrahydrofuran or an alcohol(methanol, ethanol, etc.) is used as a solvent, an inorganic base such as sodium hydrogen carbonate and sodium acetate may also be used together with such solvent. In order to convert an hydroxy group(—OH) in the compound of formula 7 to a suitable leaving group L,[methanesulfonyloxy(—OMs), p-toluenesulfonyloxy(—OTs), halogen], the hydroxy group is reacted with methanesulfonyl chloride or p-toluenesulfonyl chloride under the presence of an organic base such as triethylamine and pyridine at a temperature ranging from 0 to 50° C. to obtain the compound of formula 8 wherein the hydroxy group is substituted with leaving group L. On the other hand, the compound of formula 8 may also be obtained by converting the hydroxy group(—OH) in the compound of formula 7 to halogen according to a conventional method. In the representative example of such halogenation reaction, pyridine is added to triphenylphosphine and carbontetrabromide(J. Chem. Soc, Perkin Trans. 1, 3549, 1997) and then reacted with the compound of formula 7 to obtain the bromide compound of formula 8. The ester group of the compound of formula 8 thus obtained is reduced by using a suitable reducing agent at a temperature ranging from 0 to reflux temperature of used solvent to obtain the alcohol compound of formula 9 in a good yield. Representative reducing agent for this reaction is sodium borohydride and the reactivity of sodium borohydride increases by using it together with a lithium salt(lithium chloride or lithium bromide). When sodium azide is reacted with leaving group L in the compound of formula 9, an azidomethyl pyrrolidine compound(formula 10) is obtained. As a solvent for this reaction, dimethyl formamide(DMF) or dimethyl sulfoxide(DMSO) is preferred. In order to convert a hydroxy group in the azidomethyl pyrrolidine compound (formula 10) to suitable leaving group L[methanesulfonyloxy(—OMs), p-toluenesulfonyloxy(—OTs) or halogen], the same reaction as in the conversion of the compound of formula 7 to the compound of formula 8 is, conducted under the same condition to obtain the compound of formula 11 wherein the hydroxy group is converted to leaving group L, in a good yield. The azido group in the compound of formula 11 is reduced by using a metal catalyst such as platinum, palladium on carbon(Pd/C) and Raney nickel, or reduced by using triphenylphosphine or triphenylphosphite in an inert solvent such as tetrahydrofuran to obtain aninomethyl pyrrolidine compound(formula 12) in a good yield. When the compound of formula 12 is heated at 50 to 130° C. under the presence of a suitable base, a cyclization reaction is occurred to obtain 8-alkoxyimino-2, 6-diazaspiro[3,4]octane derivative compound of formula 13. As a solvent for use in this reaction, acetonitrile, dimethylformamide, pyridine and toluene are preferred, and preferred base include organic bases such as triethylamine, diisopropylamine, pyridine, lutidine, N,N-dimethylaniline, N,N-dimethylaminopyridine, 1,8-diazabicyclo[5,4,0]undec-7-ene(DBU), 1,5-diazabicyclo[4,3,0]nonene-5(DBN) and 1,4-diazabicyclo[2,2,2]octane(DABCO). The amine protecting group P' in the compound of formula 13 is removed, according to the kind of amine protecting group, under the same condition as in the deprotection reaction of amine protecting group P, which reaction is used for the preparation of the compound of formula 1 from the compound of formula 4 as illustrated in Reaction scheme 2, to obtain the compound of formula 3 wherein $R_3$ is H. On the other hand, the compound of formula 3 wherein $R_3$ is $C_{1-4}$ alkyl may be prepared by subjecting the exposed amine in the compound of formula 13 to a reductive alkylation reaction by using sodium cyanoborohydride as a reducing agent under a weak acidic condition with $C_{1-4}$ aldehyde, and then removing amine protecting group P', according to the kind of amine protecting group, under the substantially same condition as in the deprotection reaction of amine protecting group P, which reaction is used for the preparation of the compound of formula 1 from the compound of formula 4 as illustrated in Reaction scheme 2. Further, the compound of formula 3a, which is another starting material used in Reaction scheme 2 may be prepared by introducing an amine protecting group P, which is the same kind of protecting group as the previously defined amine protecting group P', into the compound of formula 13 to obtain the compound of formula 14 and, then, removing the amine protecting group P' in accordance with a suitable deprotection method selected from the previously presented deprotection methods depending on the kind of the amine protecting group.

The following Preparation Examples and Examples are intended to further illustrate the present invention without limiting its scope.

PREPARATION 1

1-benzyl-4-methanesulfonyloxymethyl-4-hydroxymethyl-pyrrolidine-3-one-O-methyloxime 50 g of 1-benzyl-4-ethoxycarbonyl-pyrrolidine-3-one was dissolved in 300 ml of isolpropanol and thereto 4 ml of 10% NaOH and 20.7 ml of formalin were added successively. The mixture was stirred for 30 minutes at room temperature and concentrated under the reduced pressure. 200 ml of water was added to the concentrated residue. The resulting solution was extracted twice with each 200 ml of ethylether, dried with magnesium sulfate, filtered and concentrated under the reduce pressure to give 46 g of 1-benzyl-4-hydroxymethyl-4-ethoxycarbonyl-pyrroline-3-one(yield 82.0%). The obtained compound was dissolved in 400 ml of pyridine and thereto methoxylamine hydrochloride was added and stirred for 1 hour at room temperature. The reaction mixture was concentrated under the reduced pressure, diluted with 400 ml of dichloromethane, washed with water and saline solution, dried with magnesium sulfate, filtered and concentrated under the reduced pressure to give 43 g of 1-benzyl-4-hydroxymethyl-4-ethoxycarbonyl-pyrroline-3-one-O-methyloxime(yield: 84.6%). Thus obtained compound was dissolved in a solution of 22 ml of triethylamine and 400 ml of dichloromethane and cooled to 0–5° C. and thereto 10 ml of methanesulfonylchloride was added dropwise and the reaction temperature was slowly increased up to room temperature. The reaction mixture was stirred for 1 hour, washed with water and saline solution, dried with magnesium sulfate, filtered and concentrated under the reduced pressure to give 50 g of 1-benzyl-4-methanesulfonyloxymethyl-4-ethoxycarbonyl-pyrroline-3-one-O-methyloxime(yield: 92.6%). It was dissolved in 200 ml of tetrahydrofuran and thereto 13 g of sodium borohydride and 400 ml of ethyl alcohol were added successively at room temperature and 11 g of lithium chloride was added slowly. The reaction mixture was stirred for 5 hours and poured into 300 ml of ice water. The resulting solution was adjusted to pH 5–6 with diluted hydrochloric acid, concentrated under the reduced pressure to remove most organic solvents therefrom, then extracted twice with each 200 ml of ethylether, dried with magnesium sulfate, filtered and concentrated under the reduced pressure. The residue was purified by silicagel column chromatography(ethylacetate:normal hexane=2:1) to give 42 g of the titled liquid compound(yield:94.3%).

$^1$H-NMR(CDCl$_3$, ppm): 2.54(d, 1H), 2.84(d, 1H), 2.96(s, 3H), 3.30(s, 2H), 3.60~3.71(m, 4H), 3.77(s, 3H), 4.32~4.53 (m, 2H), 7.22~7.27(m, 5H).

PREPARATION 2

1-benzyl-4-methanesulfonyloxymethyl-4-azidomethyl-pyrrolidine-3-one-O-methyloxime 42 g of 1-benzyl-4-methanesulfonyloxymethyl-4-hydroxymethyl-pyrrolidine-3-one-O-methyloxime was dissolved in 400 ml of dimethylformamide and thereto 21 g of sodium azide was added and the resulting solution was stirred for 6 hours at 110° C. The reaction mixture was concentrated under the reduce pressure, diluted with 300 ml of ethylether, washed twice with each 200 ml of water and twice with each 200 ml of saline solution, dried with magnesium sulfate, filtered and concentrated under the reduced pressure to give 31 g of 1-benzyl-4-azidomethyl-4-hydroxymethyl-1pyrrolidine-3-one-O-methyloxime (yield: 87.3%). The obtained compound and 18 ml of triethylamine were added into 300 ml of dichloromethane and cooled to 0–5° C., and thereto 9.0 ml of methanesulfonylchloride was slowly added by dropping. The reaction temperature was increased up to room temperature and the mixture was stirred for 1 hour. The reaction mixture was washed with 200 ml of water and 200 ml of saline solution, dried with magnesium sulfate, filtered and concentrated under the reduced pressure and the concentrated residue was purified by silicagel column chromatography (ethylacetate:normal hexane=1:3) to give 38.8 g of the titled compound(yield: 98.4%).

$^1$H-NMR(CDCl$_3$, ppm): 2.77(d, 2H), 2.98(s, 3H), 3.34(s, 2H), 3.57(s, 2H), 3.65(s, 2H), 3.85(s, 3H), 4.31(s, 2H), 7.22~7.27(m, 5H).

PREPARATION 3 t-butyl-6-benzyl-8-(methoxyimino)-2,6-diazaspiro[3,4]octane-2-carboxylate 10 g of 1-benzyl-4-methanesulfonyloxymethyl-4-azidomethyl-pyrrolidine-3-one-O-methyloxime was dissolved in 100 ml of ethyl acetate and thereto 5 ml of 50% Raney nickel slurry was added and the resulting mixture was stirred for 3 hours under the pressure of hydrogen. The reaction mixture was filtered and concentrated under the reduced pressure to give 8.0 g of 1-benzyl-4-methanesulfonyloxymethyl-4-aminomethyl-pyrrolidine-3-one-O-methyloxime(yield: 86%). The obtained compound was dissolved in 200 ml of acetonitrile and thereto 3.9 ml of 1,8-diazabicyclo[5,4.0]undec-7-ene was dropped, and the resulting mixture was stirred for 8 hours, concentrated under the reduce pressure, and dissolved in 150 ml of dichloromethane, washed with 100 ml of water and with 100 ml of saline solution, dried with magnesium sulfate, filtered and concentrated under the reduced pressure to give 4.0 g of 6-benzyl-2,6-diazaspiro[3,4]octane-8-one-O-methyloxime (yield: 69.3%). The obtained compound and 2.5 ml of triethylamine were dissolved in 50 ml of dichloromethane and thereto 3.9 g of di-t-butyldicarbonate. The resulting mixture was stirred for 4 hours, washed with 50 ml of water, dried with magnesium sulfate, filtered and concentrated under the reduced pressure. The concentrated residue was purified by silicagel column chromatography (ethylacetate:normal hexane:dichloromethane=3:5:1) to live 4.6 g of the titled compound(yield: 80.9%).

$^1$H-NMR(CDCl$_3$, ppm): 1.36(s, 9H), 2.80(s, 2H ), 3.24(s, 2H), 3.51(s, 2H), 3.78(d, 2H), 3.80(s, 3H), 4.24(d, 2H), 7.20~7.27(m, 5H).

PREPARATION 4 t-butyl-8-(methoxyimino)-2,6-diazaspiro[3,4]octane-2-carboxylate 4.0 g of t-butyl-6-benzyl-8-(methoxyimino)-2,6-diazaspiro[3,4]octane-2-carboxylate was dissolved in 40 ml of methanol and thereto 4.0 g of 10% Pd-C was added. The resulting mixture was stirred for 2 hours under the pressure of hydrogen at 5° C. filtered and concentrated under the reduce pressure to give 1.3 g of the titled compound(yield: 87.9%).

$^1$H-NMR(CDCl$_3$, lppm): 1.39(s, 9H), 3.18(s, 2H), 3.58(s, 2H), 3.78(d, 2H), 3.80(s, 3H), 4.05(d, 2H).

PREPARATION 5

1-benzyl-4-methanesulfonyloxymethyl-4-hydroxymethyl-pyrrolidine-3-one-O-ethyloximne.

The titled compound was prepared by the same procedure to Preparation 1.

$^1$H-NMR(CDCl$_3$, ppm): 1.21(t, 3H, J=7.07 Hz), 2.92(bs, 2H), 3.03(bs, 2H), 3.40(m, 2H), 3.72~3.75(m, 4H), 4.05~4.11(m, 2H), 4.35~4.42(m, 2H), 7.26~7.33(m, 5H)

PREPARATION 6

1-benzyl-4-methanesulfonyloxymethyl-4-azidomethyl-pyrrolidine-3-one-O-ethyloxime.

The titled compound was prepared by the same procedure to Preparation 2.

$^1$H-NMR(CDCl$_3$, ppm): 1.14(t, 3H, J=7.08 Hz), 2.63~2.72(dd, 2H, J=9.48 Hz), 2.91(s, 3H), 3.29(s, 2H), 3.51(s, 2H), 3.58(s, 2H), 4.04(q, 2H, J=7.08 Hz), 4.28(s, 2H), 7.24(m, 5H).

PREPARATION 7 t-butyl-6-benzyl-8-(ethoxyimino)-2,6-diazaspiro[3,4]octane-2-carboxylate.

The titled compound was prepared by the same procedure to Preparation 3.

$^1$H-NMR(CDCl$_3$, ppm): 1.19(m, 3H), 1.41(s, 9H), 2.85 (bs, 2H), 3.30(bs, 2H), 3.64(bs, 2H), 3.80(bs, 2H), 4.07~4.11 (m, 4H), 7.30(bs, 5H).

PREPARATION 8 t-butyl-8-(ethoxyimino)-2,6-diazaspiro[3,4]octane-2-carboxylate.

The titled compound was prepared by the same procedure to Preparation 4.

$^1$H-NMR(CDCl$_3$, ppm): 1.20(t, 3H, J=6.84 Hz), 1.38(s, 9H), 3.32(s, 2H), 3.62(s2H), 3.88(d, 2H), 4.10~4.19(m, 4H), 4.97(s, 1H).

PREPARATION 9

6-benzyl-8-(methoxyimino)-2-methyl-2,6-diazaspiro[3,4]octane.

550 mg of 6-benzyl-2,6-diazaspiro[3,4]octane-8-one-O-methyloxime was added to 10 ml of ethanol and thereto 0.4 ml of acetic acid and 176 mg of paraformaldehyde were added and the resulting mixture was stirred for 30 minutes at room temperature and thereto 370 mg of sodium cyanoborohydride was added. The resulting mixture was stirred for 16 hours at room temperature, neutralized with aqueous solution of potassium carbonate and distilled under the reduced pressure and the obtained residue was added into 50 ml of dichloromethane, washed with 50 ml of water, dried with magnesium sulfate, filtered and concentrated under the reduced pressure. The residue was purified by silicagel column chromatography(methanol:normal hexane:dichloromethane=1:10:8) to give 350 mg of the titled compound(yield: 60.1%).

$^1$H-NMR(CDCl$_3$, ppm): 2.38(s, 3H), 2.87(s, 2H) 3.19(s, 2H), 3.23(d, 2H), 3.29(d, 2H), 3.58(s, 2H), 3.89(s, 311), 7.17~7.27(m, 5H).

PREPARATION 10

8-(methoxyimino)-2-methyl-2,6-diazaspiro[3,4]octane.

340 mg of 6-benzyl-8-(methoxyimino)-2-methyl-2,6-diazaspiro[3,4]octane was dissolved in 10 ml of methanol and thereto 300 mg of 10% Pd-C was added. The resulting mixture was stirred for 2 hours at 50° C. under the pressure of hydrogen, filtered and concentrated under the reduced pressure to give 195 mg of the titled compound(yield: 85.2%).

$^1$H-NMR(CDCl$_3$, ppm): 2.33(s, 3H), 3.23~3.28(m, 4H), 3.35(d, 2H), 3.5(s, 2H), 3.86(s, 3H).

PREPARATION 11

7-[2-(t-butoxycarbonyl)-8-(methoxyimino)-2,6-diazaspiro[3,4]oct-6-yl]-1-cyclopropyl-6-fluoro-4-oxo-1,4-dihydro[1,8]naphthyridine-3-carboxylic acid.

400 mg of 1-cyclopropyl-6-fluoro-7-chloro-4-oxo-1,4-dihydro[1,8]naphthyridine-3-carboxylic acid and 84 g of t-butyl 8-(methoxyimino)-2,6diazaspiro[3,4]octane-2-carboxylate were added to 10 ml of acetonitrile and the resulting mixture was stirred for 3 hours at 45–50° C. Then the precipitated solid was filtered and dried to give 650 mg of the titled compound(yield: 93.9%).

m.p.: 278–279° C.

$^1$H-NMR(CDCl$_3$, ppm): 1.05(m, 2H), 1.27(m, 2H), 1.45 (s, 9H), 3.61~3.67(m, 1H), 3.90(s, 3H), 3.94(s, 2H), 4.25(s, 2H), 4.27(s, 2H), 4.56(s, 2H), 8.04(d, 1H, J=11.71 Hz), 8.68(s,1H).

PREPARATION 12

7-[2-(t-butoxycarbonyl)-8-(methoxyimino)-2,6-diazaspiro[3,4]oct-6-yl]-1-cyclopropyl-6-fluoro-4-oxo-1,4-dihydro-3-quinolinecarboxylic acid.

400 mg of 1-cyclopropyl-6,7-difluoro-4-oxo-1,4-dihydro-3-quinolinecarboxylic acid and 840 mg of t-butyl 8-(methoxyimino)-2,6-diazaspiro[3,4]octane-2-carboxylate were added to 10 ml of acetonitrile and the resulting mixture was refluxed for 3 hours. Then the precipitated solid was filtered and dried to give 340 mg of the titled compound (yield: 46.4%).

m.p.: 255~256° C.

$^1$H-NMR(CDCl$_3$, ppm): 1.18(bs, 2H), 1.39(m, 2H), 1.45 (s, 9H), 3.52(bs, 1H), 3.9~4.05(m, 7H), 4.27(d, 2H), 4.34(s, 2H), 7.00(d, 1H, J=7.07 Hz), 7.94(d, 1H, J=13.67 Hz), 8.64(s, 1H).

PREPARATION 13

7-[2-(t-butoxycarbonyl)-8-(methoxyimino)-2,6-diazaspiro[3,4]oct-6-yl]-1-cyclopropyl-6,8-difluoro-4-oxo-1,4-dihydro-3-quinolinecarboxylic acid.

150 mg of 1-cyclopropyl-6,7,8-trifluoro-4-oxo-1,4-dihydro-3-quinolinecarboxylic acid and 320 mg of t-butyl 8-(methoxyimino)-2,6-diazaspiro[3,4]octane-2-carboxylate were added to 10 ml of acetonitrile and the resulting mixture was refluxed for 7 hours and then cooled to room temperature. The precipitated solid was filtered and dried to give 120 mg of the titled compound(yield: 55.5%).

m.p.: 255~256° C.

$^1$H-NMR(CDCl$_3$, ppm): 1.16(s, 2H), 1.29(d, 2H), 1.44(s, 9H), 3.92~3.94(m, 6H), 4.05(s, 2H), 4.22(d, 2H), 4.38(s, 2H), 7.89(d, 1H), 8.76(s, 1H).

PREPARATION 14

7-[2-(t-butoxycarbonyl)-8-(methoxyimino)-2,6-diazaspiro[3,4]oct-6-yl]-1-cyclopropyl-6-fluoro-8-chloro-4-oxo-1,4-dihydro-3-quinolinecarboxylic acid.

300 mg of 1cyclopropyl-6,7-difluoro-8-chloro-4-oxo-1,4-dihydro-3-quinolinecarboxylic acid, 530 mg of t-butyl 8-(methoxyimino)-2,6-diazaspiro[3,4]octane-2-carboxylate and 2 g of Amberlite® IRA-420 were added to 10 ml of acetonitrile and thereto 1 ml of triethylamine was added by dropping. The resulting mixture was refluxed for 72 hours and then the resulting solid was filtered off. The filtrate was concentrated under the reduced pressure and thereto 10 ml of ethylacetate was added and the resulting solution was stirred for 4 hours. The precipitated solid was filtered and dried to give 169 mg of the titled compound(yield: 31.4%).

m.p.: 203~204° C.

$^1$H-NMR(CDCl$_3$, ppm): 1.16(bs, 2H), 1.39(d, 2H), 1,44(s, 9H), 3.92~3.94(m, 6H), 4.03(s, 2H), 4.21(d, 2H), 4.38(s, 2H), 7.88(d, 1H, J=13.19 Hz), 8.76(s, H).

PREPARATION 15

7-[2-(t-butoxycarbonyl)-8-(methoxyimino)-2,6-diazaspiro[3,4]oct-6-yl]-1-cyclopropyl-5-amino-6,8-difluoro-4-oxo-1,4-dihydro-3-quinolinecarboxylic acid.

750 mg of 1-cyclopropyl-5-amino-6,7,8-trifluoro-4-oxo-1,4-dihydro-3-quinoline-carboxylic acid, 1.05 g of t-butyl 8-(methoxyimino)-2,6-diazaspiro[3,4]octane-2-carboxylate and 4 g of Amberlite® IRA-420 were added to 20 ml of acetonitrile and thereto 2 ml of triethylamine was added by dropping. The mixture was refluxed for 5 days and then 2 ml of dimethylformamide was added thereto. The resulting mixture was stirred for 1 hour and thus precipitated solid was filtered off. The filtrate was concentrated under the reduced pressure and then to the resulting residue 10 ml of acetonitrile was added and stirred for 1 hour. The precipitated solid was filtered and dried to give 420 mg of the titled compound(yield: 30.9%).

m.p.: 256~257° C.

1H-NMR(CDCl$_3$, ppm): 1.05(s, 2H), 1.18(d, 2H), 1,44(s, 9H), 3.89~3.96(m, 6H), 3.99(s, 2H), 4.21(d, 2H), 4.34(s, 2H), 8.62(s, 1H).

PREPARATION 16

7-[2-(t-butoxycarbonyl)-8-(methoxyimino)-2,6-diazaspiro[3,4]oct -6-yl]-1-(2,4-difluorophenyl)-6-fluoro-4-oxo-1,4-dihydro-3-quinolinecarboxylic acid.

95 mg of 1-(2,4-difluorophenyl)-6,7-difluoro-4-oxo-1,4-dihydro-3-quinolinecarboxylic acid, 120 mg of t-butyl 8-(methoxyimino)-2,6-diazaspiro[3,4]octane-2-carboxylate and 400 mg of Amberlite® IRA-420 were added to 10 ml of acetonitrile and thereto 0.5 ml of triethylamine was added by dropping. The resulting mixture was refluxed for 48 hours and thus precipitated solid was filtered off. To the filtrate 5 ml of ethylether was added and the resulting mixture was stirred for 4 hours. The precipitated solid was filtered and dried to give 110 mg of the titled compound(yield: 67.8%).

m.p.: 263~264° C.

$^1$H-NMR(CDCl$_{13}$, ppm): 1,43(s, 9H), 3.64(s, 2H), 3.86~3.91(m, 2H), 3.92(s, 3H), 4.18~4.21(m, 4H), 5.91(d, 1H, J=6.84 Hz), 7.18~7.24(m, 2H), 7.48(m, 1H), 8.06(d, 1H, J=13.68), 8.54(s, 1H).

PREPARATION 17

7-[2-(t-butoxycarbonyl)-8-(methoxyimino)-2,6-diazaspiro[3,4]oct-6-yl]-1-(2,4-difluorophenyl)-6-fluoro-4-oxo-1,4-dihydro-1,8-naphthyridine-3-carboxylic acid.

110 mg of 1-(2,4-difluorophenyl)-6-fluoro-7-chloro-4-oxo-1,4-dihydro-1,8-naphthyridine-3-carboxylic acid and 120 mg of t-butyl 8-(methoxyimino)-2,6-diazaspiro[3,4] octane-2-carboxylate were added to 10 ml of acetonitrile and thereto 0.5 ml of triethylamine was added dropwise. The resulting mixture was stirred for 4 hours at 50° C. and then for 2 hours at the room temperature. The precilitated solid was filtered and dried to give 150 mg of the titled compound (yield: 79.9%).

m.p.: 230~232° C.

¹H-NMR(CDCl₃, ppm): 1.47(s, 9H), 3.82~3.92(m, 7H), 4.17~4.29(m, 4H), 7.07~7.13(m, 2H), 7.35~7.41(m, 1H), 8.12(d, 1H, J=12.20 Hz), 8.64(s, 1H).

PREPARATION 18

7-[2-(t-butoxycarbonyl)-8-(ethoxyimino)-2,6-diazaspiro[3,4]oct-6-yl]-1-cyclopropyl-6-fluoro-4-oxo-1,4-dihydro-1,8-nalphthyridine-3-carboxylic acid.

360 mg of 1-cyclopropyl-6-fluoro-7-chloro-4-oxo-1,4-dihydro-1,8-naphthyridine-3-carboxylic acid and 500 mg of t-butyl 8-(ethoxyimino)-2,6-diazaspiro[3,4]octane-2-carboxylate were added to 10 ml of acetonitrile and thereto 1 ml of triethylamine was added by dropping. The resulting mixture was stirred for 2 hours at 50° C. and then for 1 hour at the room temperature. The precipitated solid was filtered and dried to give 380 mg of the titled compound(yield: 57.9%).

m.p.: 261~262° C.

¹H-NMR(CDCl₃, ppm): 1.06(s, 2H), 1.27~1.31(m, 5H), 1.45(s, 9H), 3.64~3.66(m, 1H), 3.96(d, 2H), 4.19~4.28(m, 6H), 4.57(s, 2H), 8.08(d, 1H, J=12.20 Hz), 8.12(s, 1H).

PREPARATION 19

7-[2-(t-butoxycarbonyl)-8-(ethoxyimino)-2,6-diazaspiro[3,4]oct-6-yl]-1-cyclopropyl-5-amino-6,8-difluoro-4-oxo-1,4-dihydro-3-quinolinecarboxylic acid.

400 mg of 1-cyclopropyl-5-amino-6,7,8-trifluoro-4-oxo-1,4-dihydro-3-quinoline-carboxylic acid, 690 mg of t-butyl 8-(ethoxyimino)-2,6-diazaspiro[3,4]octane-2-carboxylate and 2 g of Amberlite® IRA-420 were added to 15 ml of acetonitrile and thereto 1.5 ml of triethylamine was dropped and the resulting mixture was refluxed for 5 days and filtered. The filtrate was concentrated under the reduced pressure and to the resulting residue 10 ml of isopropanol was added and the resulting solution was stirred for 1 hour at room temperature. The precipitated solid was filtered and dried to give 380 mg of the titled compound(yield: 51.1%).

m.p.: 235~236° C.

1H-NMR(CDCl3, ppm): 0.98(bs, 2H), 1.15~1.23(m, 5H), 1.34(s, 9H), 3.26~3.30(m, 1H), 3.86(d, 2H), 3.93(s, 2H), 4.06~4.12(m, 4H), 4.28(s, 2H), 8.53(s, 1H).

EXAMPLE 1

1-Cyclopropyl-6-fluoro-7-[8-(methoxyimino)-2,6-diazaspiro[3,4]oct-6-yl]-4-oxo-1,4-dihydro[1,8]naphthyridine-3-carboxylic acid methanesulfonate 350 mg of 7-[2-(t-buthoxycarbonyl)-8-(methoxyimino)-2,6-diazaspiro[3,4]oct-6-yl]-1-cyclopropyl-6-fluoro-4-oxo-1,4-dihydro[1,8]naphthyridine-3-carboxylic acid was dissolved in 5 ml of dichloromethane and thereto 0.6 ml of trifluoroacetic acid was dropped. The mixture was stirred for 5 hours at room temperature and thereto 10 ml of ethylether was added. It was stirred additionally for 1 hour and thus precipitated solid was filtered, dissolved in 5 ml of diluted NaOH and neutralized with diluted hydrochloric acid. The precipitate thus obtained was filtered and dried. The resulting solid was added to 5 ml of 1N-methanesulfonic acid in ethanol and stirred for 1 hour. Thus obtained precipitate was filtered and dried to give 185 g of the titled compound(yield: 47.8%).

m.p.: 228~229° C.

¹H-NMR(DMSO-d₆+CF₃COOD, ppm): 0.97(s, 2H), 1.14 (d, 2H), 2.48(s, 3H), 3.57(bs, 1H), 3.88(s, 3H), 4.06~4.17(m, 4H), 4.40(s, 2H), 4.49(s, 2H), 7.88(d, 1H, J=12.67 Hz), 8.49(s, 1H).

EXAMPLE 2

1-Cyclopropyl-6-fluoro-7-[8-(methoxyimino)-2,6-diazaspiro[3,4]oct-6-yl]-4-oxo-1,4-dihydro-3-quinolinecarboxylic acid methanesulfonate 175 mg of 7-[2-(t-butoxycarbonyl)-8-(methoxyimino)-2,6-diazspiro [3,4]oct-6-yl]-1-cyclopropyl-6-fluoro-4-oxo-1,4-dihydro-3-quinolincarboxylic acid was dissolved in 5 ml of dichloromethane and thereto 1 ml of trifluoroacetic acid was added by dropping. The resulting mixture was stirred at room temperature for 18 hours, and thereto 10 ml of ethylether was added. The resulting precipitate was filtered and dried. Thus obtained solid was dissolved in 2 ml of diluted NaOH and neutralized with diluted hydrochloric acid, and the resulting precipitate was filtered and dried. The solid thus obtained was added to 2 ml of 1N-methanesulfonic acid in ethanol and stirred at room temperature for 3 hours. The precipitate was filtered and dried to give 35 mg of the titled compound(yield: 28.5%).

m.p.: 216~217° C.

¹H-NMR(DMSO-d₆CF₃COOD, ppm): 1.04(s, 2H), 1.22 (d, 2H), 2.45(s, 3H), 3.62(bs, 1H), 3.84(s, 3H), 4.06~4.18(m, 6H), 4.23(s, 2H), 7.10(d, 1H, J=7.15 Hz), 7.76(d, 1H, J=14.27 Hz), 8.52(s, 1H).

EXAMPLE 3

1-Cyclopropyl-6,8-difluoro-7-[8-(methoxyimino)-2,6-diazaspiro[3,4]oct-6-yl]-4-oxo-1,4-dihydro-3-quinolinecarboxylic acid 150 mg of 7-[2-(t-butoxycarbonyl)-8-(methoxyimino)-2,6-diazaspiro[3,4]oct-6-yl]-1-cyclopropyl-6,8-difluoro-4-oxo-1,4-dihydro-3-quinolinecarboxylic acid was dissolved in 5 ml of dichloromethane and thereto 1 ml of trifluoroacetic acid was added dropwise. The mixture was stirred for 5 hours at room temperature and thereto 10 ml of ethylether was added. It was additionally stirred for 1 hour, and thus precipitated solid was filtered and dried. Thus obtained solid was dissolved in 5 ml of diluted sodium hydroxide and neutralized with diluted hydrochloric acid. The resulting precipitate was filtered and dried to give 115 mg of the titled compound(yield: 87.4%).

m.p.: 205~207° C.

¹H-NMR(DMSO-d₆+CF₃COOD, ppm): 1.16(s, 4H), 3.87~3.97(m, 4H), 4.06~4.33(m, 6H), 4.39(s, 2H), 7.77(d, 1H, J=13.15 Hz), 8.63(s, 1H).

EXAMPLE 4

1-Cyclopropyl-6-fluoro-8-chloro-7-[8-(methoxyimino)-2,6-diazaspiro[3,4]oct-6-yl]-4-oxo-1,4-dihydro-3-quinolinecarboxylic acid 150 mg of 7-[2-(t-butoxycarbonyl)-8-(methoxyimino)-2,6-diazaspiro[3,4]oct-6-yl]-1-cyclopropyl-6-fluoro-8-chloro-4-oxo-1,4-dihydro-3-quinolinecaboxylic acid was dissolved in 5 ml of dichloromethane and thereto 0.2 ml of trifluoroacetic acid was added dropwise. The mixture was stirred for 18 hours at room temperature, and thereto 10 ml of pyridine and 10 ml of water were added. It was distilled under the reduced pressure to remove dichloromethane and stirred for 1 hour. The precipitated solid was filtered and dried to give the titled compound(67 mg).

yield: 54.7% m.p.: 220~221° C.

$^1$H-NMR(DMSO-d$_6$+CF$_3$COOD ppm): 0.95(s, 2H), 1.16 (d, 2H), 3.89(s, 3H), 4.02~4.06(m, 4H), 4.13~4.23(m, 4H), 4.34(bs, 1H), 7.92(d, 1H, J=12.44 Hz)

EXAMPLE 5

1-Cyclopropyl-5-amino-6,8-difluoro-7-[8-(methoxyimino)-2,6-diazaspiro[3,4]oct-6-yl]-4-oxo-1,4-dihydro-3-quinolinecarboxylic acid methanesulfonate 420 mg of 7-[2-(t-Butoxycabonyl)-8-(methoxyimino)-2,6-diazaspiro[3,4]oct-6-yl]-1-cyclopropyl-5-amino-6,8-difluoro-4-oxo-1,4-dihydro-3-quinolinecarboxylic acid was dissolved in 10 ml of dichloromethane and thereto 1 ml of trifluoroacetic acid was added dropwise. The mixture was stirred at room temperature for 18 hours, and thereto 10 ml of pyridine was added. It was distilled under the reduced pressure. The residue was purified by silica gel chromatography(chloroform:methyl alcohol:water-6:2:0.2). Thus obtained solid was added to 2 ml of 1N-methansulfonic acid in ethanol, stirred for 3 hours at room temperature. The precipitated solid was filtered and dried to give the titled compound(165 mg)

yield: 39.6% m.p.: 238~239° C.

$^1$H-NMR(DMSO-d$_6$+CF$_3$COOD, ppm): 1.09(bs, 4H), 2.49(s, 3H), 3.89(s, 3H), 3.92~3.99(m, 1H), 4.08~4.20 (m, 6H), 4.35(s, 2H), 8.50(s, 1H).

EXAMPLE 6

1-(2,4-Difluorophenyl)-6-fluoro-7-[8-(methoxyimino)-2,6-diazaspiro[3,4]oct-6-yl]-4-oxo-1,4-dihydro-3-quinolinecarboxylic acid dimethanesulfonate 90 mg of 7-[2-(t-butoxycarbonyl)-8-(methoxyimino)-2,6-diazaspiro[3,4]oct-6-yl]-1-(2,4-difluorophenyl)-6-fluoro-4-oxo-1,4-dihydro-3-quinolinecarboxylic acid was dissolved in 5 ml of dichloromethane and thereto 0.1 ml of trifluoroacetic acid was added by dropping. The mixture was stirred at room temperature for 12 hours and thereto 5 ml of pyridine was added. The mixture was distilled under the reduced pressure to remove dichloromethane and thereto 5 ml of water was added. It was stirred at room temperature for 2 hours. The resulting precipitatte was filtered and dried, and added to 2 ml of 1N-methansulfonic aicid in ethanol and stirred at room temperature for 1 hour. Thus precipitated solid was filtered and dried to give the titled compound(45 mg).

yield: 43.1% m.p.: 216~217° C.

$^1$H-NMR(DMSO-d$_6$+CF$_3$COOD, ppm): 2.49(s, 6H), 3.74~4.09(m, 11H), 5.93(d, 1H), 7.24(m, 1H), 7.45(m, 1H), 7.88(m, 1H), 7.89(d, 1H, J=14.4 Hz), 8.60(s, 1H).

EXAMPLE 7

1-(2,4-Difluorophenyl)-6-fluoro-7-[8-(methoxyimino)-2,6-diazaspiro[3,4]oct-6-yl]-4-oxo-1,4-dihydro-1,8-nalphthyridine-3-carboxylic acid methanesulfonate 140 mg of 7-[2-(t-Butoxycarbonyl)-8-(methoxyimino)-2,6-diazaspiro[3,4]oct-6-yl]-1-(2,4-difluorophenyl)-6-fluoro-4-oxo-1,4-dihydro-1,8-nai)hthyridine-3-carboxylic acid was dissolved in 5 ml of dichloromethane and thereto 0.2 ml of trifluoroacetic acid was added by dropping. The mixture was stirred at room temperature for 12 hours and thereto 5 ml of pyridine was added. It was distilled under the reduced pressure to remove dichloromethane and thereto 5 ml of water was added. It was stirred at room temperature for 2 hours. The resulting precipitate was filtered and dried. Thus obtained solid was added to 2 ml of 1N-methansulfonic acid in ethanol and stirred at room temperature for 1 hour. The precipitate was filtered and dried to give the titled compound (95 mg).

yield: 68.3% m.p.: 201~202° C.

$^1$H-NMR(DMSO-d$_6$+CF$_3$COOD, ppm): 2.49(s, 3H), 3.85 (s, 3H), 3.88~4.10(m, 8H), 7.23~7.26(m, 1H), 7.40~7.4(m, 1H), 7.70~7.76(m, 1H), 8.07(d, 1H, J=12.44 Hz), 8.76(s, 1H).

EXAMPLE 8

1-Cyclopropyl-6-fluoro-7-[8-(ethoxyimino)-2,6-diazaspiro[3,4]oct-6-yl]-4-oxo-1,4-dihydro-1,8-naphthyridine-3-carboxylic acid methanesulfonate 380 mg of 7-[2-(t-Butoxycarbonyl)-8-(ethoxyimino)-2,6-diazaspiro[3,4]oct-6-yl]-1-cyclopropyl-6-fluoro-4-oxo-1,4-dihydro-1,8-naphthyridine-3-carboxylic acid was dissolved in 5 ml of dichloromethane and thereto 0.6 ml of trifluoroacetic acid was added dropwise. The mixture was stirred at room temperature for 12 hours and thereto 3 ml of pyridine was added. It was distilled under the reduced pressure to remove dichloromethane and 1 ml of water was added thereto. It was stirred at room temperature for 2 hours. Thus precipitated solid was filtered and dried. The resulting solid was added to 2 ml of 1N-methansulfonic acid in ethanol and stirred at room temperature for 1 hour. The precipitate was filtered and dried to give 220 mg of the titled compound (yield: 58.3%).

m.p.: 211~212° C.

1H-NMR(DMSO-d$_6$+CF$_3$COOD, ppm): 1.02(bs, 2H), 1.19~1.28(m, 5H), 2.48(s, 3H), 3.63~3.68(m, 1H), 4.06~4.20(m, 5H), 4.38(s, 2H), 4.51(s, 2H), 7.97(d, 1H, J=12.44 Hz), 8.55(s, 1H).

EXAMPLE 9

1-Cyclopropyl-5-amino-6,8-difluoro-7-[8-(ethoxyimino)-2,6-diazaspiro[3,4]-oct- 6-yl]-4-oxo-1,4-dihydro-3-quinolinecarboxylic acid methanesulfonate 380 mg of 7-[2-(t-Butoxycabonyl)-8-(ethoxyimino)-2,6-diazaspiro[3,4]oct-6-yl]-1-cyclopropyl-5-amino-6,8-difluoro-4-oxo-1,4-(dihydro-3-quinolinecarboxylic acid was dissolved in 10 ml of dichloromethane and thereto 0.7 ml of trifluoroacetic acid was dropped. The mixture was stirred at room temperature for 18 hours and thereto 10 ml of pyridine was added. It was distilled under the reduced pressure to remove the solvent. The residue was purified by silica gel chromatography(chloroform:methyl alcohol:water= 6:2:0.2). Thus obtained solid was added to 1.5 ml of 1N-methansulfonic acid in ethanol and stirred at room temperature for 3 hours. The resulting precipitate was filtered and dried to give 180 mg of the titled compound(yield: 47.1%).

m.p.: 221~222° C.

¹H-NMR(DMSO-d₆+CF₃COOD, ppm): 0.96~1.02(m, 4H), 1.15(t, 3H, J=7.08 Hz), 2.49(s, 3H), 3.87(d, 1H), 3.98~4.12(m, 8H), 4.22(s, 2H), 8.42(s, 1H).

EXAMPLE 10

1-Cyclopropyl-6-fluoro-7-[8-(methoxyimino)-2-methyl-2,6-diazaspiro[3,4]oct-6-yl]-4-oxo-1,4-dihydro-1,8-naphthyridine-3-carboxylic acid 300 mg of 1-Cyclopropyl-6-fluoro-7-[8-(methoxyimino)-2,6-diazaspiro[3,4]oct-6-yl]-4-oxo-1,4-dihydro-1,8-naphthyridine-3-carboxylic acid was added to 10 ml of ethanol, and thereto 0.2 ml of acetic acid was dropped and 42 mg of p-formaldehyde was added. The mixture was stirred at room temperature for 30 minutes, and thereto 85 mg of sodium cyanoborohydride was added. It was stirred at room temperature for 2 hours. The resulting precipitate was filtered and dried to give 260 mg of the titled compound (yield: 83.7%).

m.p.: 225~227° C.

¹H-NMR(DMSO-d₆+CF₃COOD, ppm): 0.95(s, 2H), 1.16 (d, 2H), 2.49(s, 3H), 3.58~3.61(m, 1H), 3.87(s, 3H), 4.08~4.18(m, 4). 4.34(s, 2H), 7.93(d, 1H, J=12.43 Hz), 8.51(s, 1H).

EXAMPLE 11

1-Cyclopropyl -5-amino-6,8-difluoro-7-[8-(methoxyimino)-2-methyl-2,6-diazaspiro[3,4]oct-6-yl]-4-oxo-1,4-dihydro-3-quinolinecarboxylic acid 300 mg of 1-Cyclopropyl-5-amino-6,8-difluoro-7-[8-(methoxyimino)-2,6-diazaspiro[3,4]oct-6-yl]-4-oxo-1,4-dihydro-3-quinolinecarboxylic acid was added to 10 ml of ethanol, and thereto 0.2 ml of acetic acid was dropped and 44 mg of p-formaldehyde was added. It was stirred at room temperature for 30 minutes and thereto 91 mg of sodium cyanoborohydride was added. It was stirred at room temperature for 2 hours. The resulting precipitate was filtered to give 280 mg of the titled compound(yield 90.4%).

mp.: 220~222° C.

²H-NMR(DMSO-d₆+Cr₃COOD, ppm): 1.15~1.23(m, 4H), 2.64(s, 3H), 4.05(s, 3H), 4.06~4.10(m, 1H), 4.20~4.39 (m, 6H), 4.47(s, 2H), 8.62(s, 1H).

Experimental 1.

In Vitro Antibacterial Activity Test

In order to evaluate the in vitro antibacterial activities of the compounds prepared in examples according to the present invention the minimum inhibitory concentrations (MIC, μg/ml) were measured by the 2-fold agar dilution method(Hoechst 345) using the Muller-Hinton agar. $10^7$ cfu/ml of bacteria were inoculated and cultured for 18 hours at 37° C. and then the antibacterial activities were measured. For the methicillin resistant strains the activities were measured after 48 hours of cultivation 30 at 30° C. Hoechst Standard strains were used for the testings. The result is shown in the next tables 1 and 2.

TABLE 1

| In vitro Antibacterial Activity (μg/ml) | | | | |
|---|---|---|---|---|
| Strains\Compounds | Example 1 | Example 2 | Example 3 | Example 4 |
| *Streptococcus pyogens* 308A | 0.098 | 0.195 | 0.391 | 0.195 |
| *Streptococcus pyogens* 77A | 0.007 | 0.007 | 0.025 | 0.013 |
| *Streptococcus faecium* MD 8b | 0.049 | 0.098 | 0.098 | 0.098 |
| *Staphylococcus aureus* SG511 | 0.007 | 0.013 | 0.025 | 0.013 |
| *Staphylococcus aureus* 285 | 0.025 | 0.049 | 0.049 | 0.049 |
| *Staphylococcus aureus* 503 | 0.025 | 0.049 | 0.098 | 0.025 |
| *Esherichia coli* 078 | 0.013 | 0.025 | 0.098 | 0.025 |
| *Esherichia coli* DC0 | 0.195 | 0.198 | 0.391 | 0.391 |
| *Esherichia coli* DC2 | 0.025 | 0.013 | 0.025 | 0.049 |
| *Esherichia coli* TEM | 0.025 | 0.049 | 0.049 | 0.049 |
| *Esherichia coli* 1507E | 0.025 | 0.049 | 0.049 | 0.049 |
| *Pseudomonas aeruginosa* 9027 | 0.781 | 0.781 | 1.563 | 0.781 |
| *Pseudomonas aeruginosa* 1592E | 0.391 | 0.391 | 0.781 | 0.781 |
| *Pseudomonas aeruginosa* 1771 | 0.391 | 0.391 | 1.563 | 0.781 |
| *Pseudomonas aeruginosa* 1771M | 0.391 | 0.391 | 0.781 | 0.391 |
| *Salmonella typhimurium* | 0.013 | 0.025 | 0.025 | 0.025 |
| *Klebsiella oxytoca* 1082E | 0.004 | 0.007 | 0.007 | 0.004 |
| *Klebsiella aerogenes* 1522E | 0.049 | 0.098 | 0.098 | 0.098 |
| *Enterobacter clocae* P99 | 0.025 | 0.049 | 0.049 | 0.049 |
| *Enterobacter clocae* 1321E | 0.013 | 0.025 | 0.025 | 0.025 |
| Strains\Compounds | Example 5 | Example 6 | Example 77 | Example 8 |
| *Streptococcus pyogens* 308A | 0.025 | 0.195 | 0.195 | 0.098 |
| *Streptococcus pyogens* 77A | <0.002 | 0.013 | 0.013 | 0.007 |
| *Streptococcus faecium* MD 8b | 0.025 | 0.195 | 0.098 | 0.098 |
| *Staphylococcus aureus* SG511 | <0.002 | 0.049 | 0.013 | 0.007 |
| *Staphylococcus aureus* 285 | 0.007 | 0.098 | 0.049 | 0.025 |
| *Staphylococcus aureus* 503 | <0.002 | 0.049 | 0.025 | 0.013 |
| *Esherichia coli* 078 | <0.002 | 0.049 | 0.049 | 0.013 |
| *Esherichia coli* DC0 | 0.098 | 0.781 | 0.781 | 0.391 |
| *Esherichia coli* DC2 | 0.013 | 0.098 | 0.098 | 0.025 |

TABLE 1-continued

In vitro Antibacterial Activity (μg/ml)

| | | | | |
|---|---|---|---|---|
| Esherichia coli TEM | 0.013 | 0.195 | 0.098 | 0.025 |
| Esherichia coli 1507E | 0.007 | 0.195 | 0.195 | 0.049 |
| Pseudomonas aeruginosa 9027 | 0.781 | 3.125 | 1.563 | 1.563 |
| Pseudomonas aeruginosa 1592E | 0.391 | 1.563 | 1.563 | 0.781 |
| Pseudomonas aeruginosa 1771 | 0.391 | 1.563 | 1.563 | 0.781 |
| Pseudomonas aeruginosa 1771M | 0.195 | 1.563 | 0.781 | 0.781 |
| Salmonella typhimurium | <0.002 | 0.049 | 0.049 | 0.013 |
| Klebsiella oxytoca 1082E | <0.002 | 0.013 | 0.013 | 0.004 |
| Klebsiella aerogenes 1522E | 0.025 | 0.391 | 0.195 | 0.098 |
| Enterobacter clocae P99 | 0.007 | 0.098 | 0.098 | 0.025 |
| Enterobacter clocae 1321E | 0.004 | 0.098 | 0.049 | 0.025 |

| Strains\Compounds | Example 9 | Example 10 | Example 11 | Ciprofloxacin | Sparfloxacin |
|---|---|---|---|---|---|
| Streptococcus pyogens 308A | 0.025 | 0.098 | 0.013 | 3.125 | 0.391 |
| Streptococcus pyogens 77A | 0.004 | 0.013 | 0.004 | 0.781 | 0.195 |
| Streptococcus faecium MD 8b | 0.049 | 0.098 | 0.049 | 0.391 | 0.391 |
| Staphylococcus aureus SG511 | <0.002 | 0.013 | <0.002 | 0.195 | 0.098 |
| Staphylococcus aureus 285 | 0.007 | 0.049 | 0.007 | 0.781 | 0.049 |
| Staphylococcus aureus 503 | <0.002 | 0.025 | 0.004 | 0.391 | 0.049 |
| Esherichia coli 078 | 0.004 | 0.013 | <0.002 | 0.004 | 0.004 |
| Esherichia coli DC0 | 0.195 | 0.391 | 0.098 | 0.195 | 0.195 |
| Esherichia coli DC2 | 0.013 | 0.049 | 0.013 | 0.049 | 0.025 |
| Esherichia coli TEM | 0.013 | 0.049 | 0.013 | 0.007 | 0.013 |
| Esherichia coli 1507E | 0.013 | 0.049 | 0.013 | 0.007 | 0.025 |
| Pseudomonas aeruginosa 9027 | 0.781 | 0.781 | 0.781 | 0.195 | 0.781 |
| Pseudomonas aeruginosa 1592E | 0.781 | 0.781 | 0.781 | 0.195 | 0.781 |
| Pseudomonas aeruginosa 1771 | 0.781 | 0.781 | 0.781 | 0.195 | 0.781 |
| Pseudomonas aeruginosa 1771M | 0.391 | 0.781 | 0.391 | 0.049 | 0.195 |
| Salmonella typhimurium | 0.007 | 0.049 | 0.007 | 0.007 | 0.007 |
| Klebsiella oxytoca 1082E | <0.002 | 0.007 | <0.002 | <0.002 | <0.002 |
| Klebsiella aerogenes 1522E | 0.049 | 0.098 | 0.049 | 0.013 | 0.025 |
| Enterobacter clocae P99 | 0.007 | 0.049 | 0.013 | 0.007 | 0.007 |
| Enterobacter clocae 1321E | 0.007 | 0.025 | 0.004 | <0.002 | 0.004 |

TABLE 2

In vitro Antibacterial Activity against resistant strains.

(μg/ml)

| Strains\Compounds | Example 1 | Example 5 | Example 9 | Example 11 | Ciprofloxacin | Sparfloxacin |
|---|---|---|---|---|---|---|
| Staphylococcus aureus 88E | 0.049 | 0.007 | 0.007 | 0.007 | 0.781 | 0.098 |
| Staphylococcus aureus 121E | 0.049 | 0.013 | 0.013 | 0.013 | 0.781 | 0.098 |
| Staphylococcus aureus 208E | 0.049 | 0.007 | 0.013 | 0.013 | 0.781 | 0.098 |
| Staphylococcus aureus 256E | 0.025 | 0.007 | 0.013 | 0.007 | 0.781 | 0.098 |
| Staphylococcus aureus 690E | 0.025 | 0.007 | 0.007 | 0.007 | 0.391 | 0.049 |
| Staphylococcus aureus 692E | 0.025 | 0.004 | 0.007 | 0.007 | 0.391 | 0.049 |
| Staphylococcus aureus 693E | 0.049 | 0.007 | 0.013 | 0.013 | 0.391 | 0.049 |
| Staphylococcus aureus 694E | 0.049 | 0.007 | 0.013 | 0.013 | 0.391 | 0.098 |
| Staphylococcus aureus 695E | 0.049 | 0.007 | 0.013 | 0.013 | 0.391 | 0.049 |
| Staphylococcus aureus 697E | 0.013 | <0.002 | 0.004 | 0.004 | 0.391 | 0.049 |
| Staphylococcus aureus 701E | 0.049 | 0.007 | 0.013 | 0.013 | 0.391 | 0.098 |
| Staphylococcus aureus 703E | 0.049 | 0.007 | 0.013 | 0.013 | 0.391 | 0.098 |
| Staphylococcus aureus 179 | 0.781 | 0.098 | 0.098 | 0.195 | 12.500 | 6.250 |
| Staphylococcus aureus 241 | 0.781 | 0.098 | 0.098 | 0.195 | 12.500 | 6.250 |
| Staphylococcus aureus 293 | 0.781 | 0.098 | 0.098 | 0.195 | 12.500 | 6.250 |
| Staphylococcus aureus 303 | 0.781 | 0.098 | 0.098 | 0.195 | 12.500 | 3.125 |
| Staphylococcus aureus 8236 | 0.781 | 0.098 | 0.098 | 0.195 | 12.500 | 6.250 |
| Staphylococcus epidermidis 178 | 1.563 | 0.391 | 0.391 | 0.781 | 50.000 | 6.250 |
| Staphylococcus epidermidis 291 | 1.563 | 0.391 | 0.391 | 0.781 | 50.000 | 6.250 |

Experimental 2.
Acute Toxicity Test

In the acute toxicity test of the quinolonecarboxylic acid derivatives prepared in examples according to the present invention ICR mice of 23–25 g were used. Each group of mice comprised 5 male and 5 female mice and each sample compound was distributed into 5 doses.

After mice were starved for 24 hours only with water, samples diluted in 0.2 ml of 0.1N NaOH and respectively adjusted to a predetermined dose were injected into the vein of mouse tails. After 1 hour from the injection mice was fed and then during 14 days lethality was observed.

As the result, the values of $LD_{50}$(mg/kg) of quinolonecarboxylic acid derivatives and its pharmaceutically acceptable salts according to the invention were of over 320, whereby it was proved that the compounds of the invention have high safety as antibacterial agents.

EFFECT OF THE INVENTION

The quinolonecarboxylic acid derivatives according to the present invention are very safe compounds as having very low toxicity, and they have more improved antibacterial activity than that of known quinolone antibacterial agents against gram positive bacteria, good antibacterial activity against gram negative bacteria and especially excellent antibacterial activity against methicillin resistant bacteria and known quinolone resistant bacteria.

Accordingly, the quinolonecarboxylic acid derivatives of the present invention are very useful as antibacterial agents.

What is claimed is:

1. A quinolonecarboxylic acid derivative represented by following formula 1, or a pharmaceutically acceptable salt or an isomer thereof:

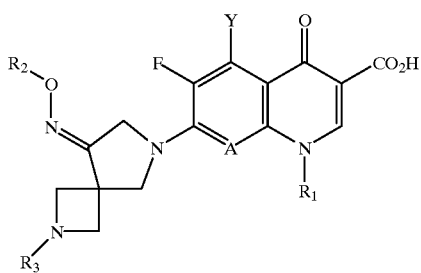

1

Wherein, A is N; Y is H or amino; $R_1$ is cyclopropyl or 2,4-difluorophenyl; $R_2$ is $C_{1-4}$ alkyl; and $R_3$ is H or $C_{1-4}$ alkyl.

2. A process for preparing a quinolonecarboxylic acid derivative, which comprises conducting coupling reaction of the compound of formula 2 with the compound of formula 3 under the presence of an acid acceptor to obtain the compound of formula 1:

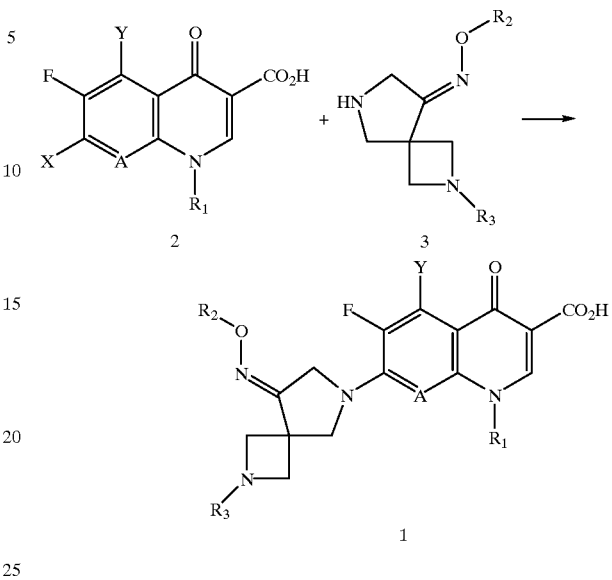

Wherein, A is N; Y is H or amino; $R_1$ is cyclopropyl or 2,4-difluorophenyl; $R_2$ is $C_{1-4}$ alkyl; $R_3$ is H or $C_{1-4}$ alkyl; and X is a halogen atom.

3. The process of claim 2, wherein an ion-exchange resin selected from the group consisting of Amberlite® IRA-420, Amberlite® IRA-900 and Amberlite® IRA-64 is used for increasing the reactivity of the condensation reaction.

* * * * *